(12) United States Patent
Sotkovsky

(10) Patent No.: US 12,364,450 B2
(45) Date of Patent: Jul. 22, 2025

(54) PORTABLE X-RAY DETECTOR HOLDER AND POSITIONER

(71) Applicant: Ryan Sotkovsky, Port St. Lucie, FL (US)

(72) Inventor: Ryan Sotkovsky, Port St. Lucie, FL (US)

( * ) Notice: Subject to any disclaimer, the term of this patent is extended or adjusted under 35 U.S.C. 154(b) by 369 days.

(21) Appl. No.: 17/739,229

(22) Filed: May 9, 2022

(65) Prior Publication Data
US 2022/0354445 A1 Nov. 10, 2022

Related U.S. Application Data

(60) Provisional application No. 63/185,408, filed on May 7, 2021.

(51) Int. Cl.
*A61B 6/00* (2024.01)
*A61B 6/42* (2024.01)

(52) U.S. Cl.
CPC ............ *A61B 6/4429* (2013.01); *A61B 6/42* (2013.01); *A61B 6/4405* (2013.01)

(58) Field of Classification Search
CPC .... F16M 11/10; F16M 11/2014; F16M 11/04; F16M 11/24; F16M 11/06; F16M 11/12; F16M 11/041; F16M 11/08; F16M 11/105; F16M 11/18; F16M 11/2071; F16M 13/02; F16M 13/022; F16M 13/025; F16M 2200/044; F16M 2200/063; F16M 2200/066; F16M 2200/022; F16M 2200/06; F16M 2200/065
See application file for complete search history.

(56) References Cited

U.S. PATENT DOCUMENTS

| | | | | | |
|---|---|---|---|---|---|
| 5,533,090 | A | * | 7/1996 | Nyzen | A61B 6/4429 378/197 |
| 5,799,917 | A | * | 9/1998 | Li | F16M 13/022 248/921 |
| 6,554,472 | B1 | * | 4/2003 | Dietz | A61B 6/4458 378/197 |
| 9,256,911 | B1 | * | 2/2016 | Parsons | F16M 11/10 |
| 9,706,843 | B2 | * | 7/2017 | Hung | F16M 11/24 |
| 2004/0079849 | A1 | * | 4/2004 | Rudolf | F16M 11/14 248/917 |

(Continued)

*Primary Examiner* — David J Makiya
*Assistant Examiner* — Soorena Kefayati
(74) *Attorney, Agent, or Firm* — The Rapacke Law Group, P.A.

(57) ABSTRACT

Disclosed are devices and methods for facilitating the obtaining of radiologic images. Some embodiments of the disclosed devices are directed to a portable x-ray holder and positioner having a base, an arm coupled to the base, and an x-ray holding mechanism coupled to the arm. In certain embodiments, the arm is configured to be rotatable and extendable. In one embodiment, the device includes a hinge coupled to the base and/or to the arm. In some embodiments, the x-ray holding mechanism includes one or more brackets coupled to the arm. In certain embodiments, the arm has a first part configured to receive a second part within the first part, and the second part is configured to be telescoped out of the first part. In one embodiment, a fastening mechanism is provided that cooperates with the hinge and the arm to maintain a desired angular position of the arm.

8 Claims, 7 Drawing Sheets

(56) References Cited

U.S. PATENT DOCUMENTS

| | | | |
|---|---|---|---|
| 2013/0193295 A1* | 8/2013 | Lui | A61B 6/4283 |
| | | | 248/416 |
| 2015/0030135 A1* | 1/2015 | Choi | A61B 6/04 |
| | | | 378/189 |
| 2015/0085991 A1* | 3/2015 | Futterer | F16M 13/027 |
| | | | 248/550 |
| 2018/0055465 A1* | 3/2018 | Nakayama | A61B 6/4452 |
| 2019/0200944 A1* | 7/2019 | Ahearn | A61B 6/4411 |
| 2020/0155089 A1* | 5/2020 | Reina | A61B 6/4291 |
| 2022/0054099 A1* | 2/2022 | Han | F16M 11/128 |

\* cited by examiner

PORTABLE X-RAY DETECTOR HOLDER AND POSITIONER

CROSS-REFERENCE TO RELATED APPLICATIONS

The present application claims priority to U.S. Provisional Patent Application No. 63/185,408 filed May 7, 2021, entitled "PORTABLE X-RAY DETECTOR HOLER AND POSITIONER," which is hereby incorporated by reference in its entirety.

TECHNICAL FIELD

Embodiments of the invention relate generally to devices and methods for facilitating the obtaining of radiologic images. In particular, embodiments of the invention are directed to devices and methods for holding and positioning an x-ray detector at a desired position to improve patient comfort and increase the efficiency of obtaining radiologic images. In some embodiments, the invention is most particularly directed to a portable x-ray detector holder and positioner having a rotatable and extendable arm.

BACKGROUND

Current x-ray detector holders tend to be bulky, heavy, and only hold the x-ray detector in only one position at a 90-degree angle. Technicians are allowed to use only these holders in the x-ray room, and it is not feasible to take such holders on portables due to their size, weight, and the inability to adjust the angle of the x-ray detector. Another method technicians currently use, especially during portable exams, is to wedge towels, sheets, blankets, and pillows underneath the x-ray detector to get the desired position angle to make the patient comfortable and allow the technician to perform the exam.

Alternate known methods include a stationary x-ray detector holder. This apparatus is heavy, bulky, and only positions the x-ray detector at a 90-degree angle. This method and device are limited because the device is only used inside the x-ray room to perform cross-table lateral positions in lower extremity trauma patient situations.

Another alternative is to prop folded up sheets, blankets, towels, pillows, or the like, behind or underneath the x-ray detector to obtain a position (including angle) that is comfortable for the patient. This method is limited because the x-ray detector is not supported in the same position and allows the x-ray detector to shift while taking the images, which cause repeats, more exposure to the patient, and a longer exam time.

SUMMARY OF THE INVENTION

In one embodiment, the invention concerns a portable x-ray detector holder and positioner. The x-ray detector holder and positioner can include a base plate; a hinge coupled to the base plate; a base arm coupled to the hinge; a fastening mechanism for facilitating an angular adjustment of the base arm relative to the base, wherein the fastening mechanism is coupled to the base arm and/or to the hinge; an extending arm configured to be received in the base arm and to be telescoped out of the base arm; a fastening mechanism for facilitating a length adjustment of the extending arm relative to the base arm, wherein the fastening mechanism is coupled to the base arm and/or to the extending arm; and an x-ray detector holding mechanism coupled to the base arm and/or to the extending arm for holding an x-ray detector.

In some embodiments, the fastening mechanism for facilitating an angular adjustment comprises a screw, and the fastening mechanism for facilitating a length adjustment comprises a screw. In certain embodiments, the x-ray detector holding mechanism comprises one or more brackets coupled to the base arm and/or to the extending arm.

In another aspect, the invention is directed to a method of obtaining radiologic images. In one embodiment the method involves providing an x-ray detector holder and positioner. The x-ray detector holder and positioner can include a base; a rotatable and extendable arm coupled to the base; and an x-ray detector holding mechanism coupled to the arm. The method can further involve adjusting an angle of the arm to a desired angle; adjusting a length of the arm to a desired length; attaching an x-ray detector to the x-ray detector holding mechanism; and positioning the x-ray detector holder and positioner relative to a patient to facilitate obtaining the radiologic image.

In certain embodiment, the x-ray detector holder and positioner of the method further comprises a hinge and at least one bracket coupled to the arm. In some embodiments, the arm of the method comprises a first structure configured to receive a second structure, wherein the second structure is configured to be telescoped out of the first structure.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein.

DETAILED DESCRIPTION

Figure 1:
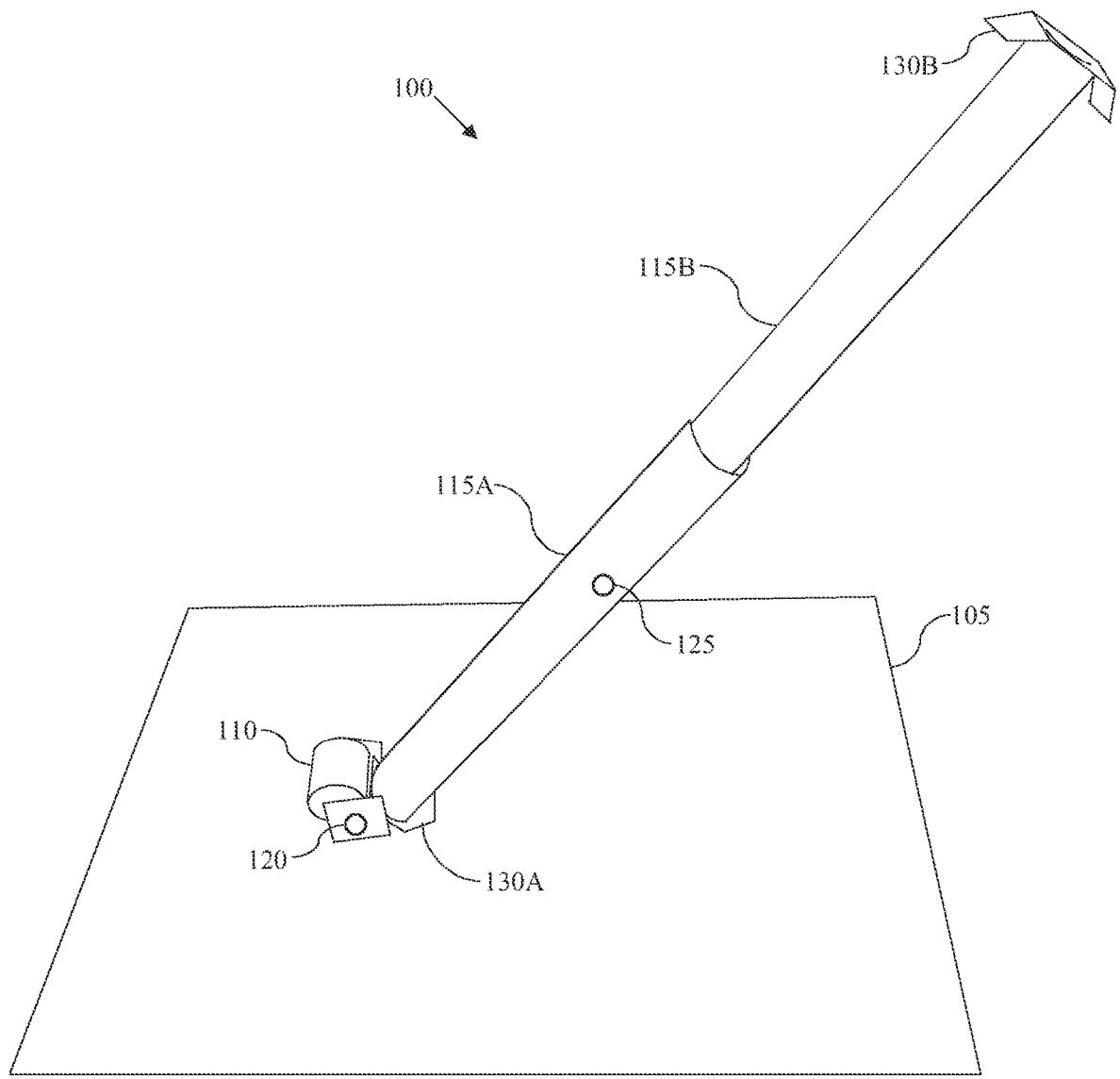
FIG. 1 illustrates a perspective view of an x-ray detector holder in accordance with one embodiment of the invention.

The specific details of the single embodiment or variety of embodiments described herein are set forth in this application. Any specific details of the embodiments are used for demonstration purposes only, and no unnecessary limitation or inferences are to be understood therefrom.

Before describing in detail exemplary embodiments, it is noted that the embodiments reside primarily in combinations of components related to the system. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In some embodiments, the invention is directed to an x-ray detector holder and positioner that facilitates adjusting the angle and position of the x-ray detector. Known x-ray detector holders are typically stationary and hold the x-ray detector only at a 90-degree angle. Disclosed embodiments of the invention facilitate adjusting the angle of the x-ray detector at least from 0- to 90-degrees.

In certain embodiments, the x-ray detector holder and positioner has an advantageous size and portability. Known x-ray detector holders are large, heavy, and awkward in shape, which limits where an x-ray detector holder can be used and/or stored. Inventive embodiments of the x-ray detector holder and positioner disclosed here are lightweight and ergonomically designed so that that the x-ray detector holder and positioner can be transported and used in a variety of locations or settings (for example, x-ray room, portable machine, trauma, and the like). Some embodiments of the x-ray detector holder and positioner disclosed herein are convenient to store when not in use, leaving room for other equipment.

Embodiments of the invention provide various advantages over known methods. Some embodiments of the invention are lightweight and therefore easier to carry than current x-ray detector holders. Certain embodiments of the invention are ergonomic and enable the technician to easily store the x-ray holder and positioner, whether on a portable machine or in an x-ray room. Advantageously, certain embodiments of invention disclosed herein facilitate adjusting the angle of the x-ray detector, thereby facilitating improving the comfort of the patient and allowing the technician to perform the exam more efficiently. The more comfortable the patient is, the more likely that the technician will obtain clear and sharp images for a physician to read, thereby improving the patient's care and diagnosis.

In one embodiment, the x-ray detector holder and positioner can be used in various imaging settings, such as a hospital, outpatient center, urgent care, orthopedic offices, and more.

In some embodiments, the invention is directed to a durable, lightweight x-ray holder and positioner to assist radiologic technicians and patients during exams. In some embodiments, the x-ray holder and positioner is configured to hold an x-ray detector at a specific place and angle to improve the comfort of a patient and to enable the technician to more easily position the patient and to more efficiently perform an exam.

In some embodiments, the x-ray holder and positioner is configured to be ergonomic and lightweight to use in the x-ray room, on portables, and in trauma exams. In certain embodiments, the x-ray holder and positioner is configured to provide a steady foundation, so the x-ray detector remains in position throughout the exam; and the x-ray detector holder and positioner enables the technician to adjust the angle of the x-ray detector's position to assist the patient in maintaining proper radiographic positioning and to facilitate a more efficient exam for the technician.

Referencing FIG. 1, in one embodiment x-ray holder and positioner 100 includes base 105. In some embodiments, base 105 is rectangular and measures approximately 11-in by 16-in. In certain embodiments, x-ray holder and positioner 100 includes hinge 110, coupled to base 105, for supporting and positioning angularly moveable arm 115A, 115B. In one embodiment a fastening mechanism such as hinge screw 120 is coupled to hinge 110 and/or to arm 115A, 115B to facilitate setting and maintaining a desired angle of arm 115A, 115B. In certain embodiments, arm 115A, 115B, hinge 110, and hinge screw 120 are configured to enable adjusting the angle of arm 115A, 115B through a range of at least 0-degrees (see FIG. 2) to 90-degrees (see FIG. 4) relative to base 105.

In one embodiment, arm 115A, 115B is an extendable structure having base arm 115A and extending arm 115B. In some embodiments, both base arm 115A and extending arm 115B can be about 10-in long; however, in certain embodiments base arm 115A can have a length that is different from the length of extending arm 115B. In certain embodiments, base arm 115A is configured to receive within extending arm 115B, such that extending arm 115B substantially fits completely within base arm 115A and can be telescoped out of base arm 115A a length substantially as long as the length of extending arm 115B. In some embodiments, there are multiples of extending arm 115B that are coupled to one another to provide any suitable extension desired for the task of obtaining radiologic images. In certain embodiments, base arm 115A and extending arm 115B are structures that can be coupled to each other at varying lengths, without extending arm 115B being necessarily received within base arm 115A.

In some embodiments, a fastening mechanism such as arm screw 125 can be provided to secure extending arm 115B to base arm 115A to hold extending arm 115B at a desired length while in use. In one embodiment, one end of base arm 115A is provided with bracket 130A and one end of arm 115B is provided with bracket 130B for holding an x-ray detector (not shown) in place while in use.

X-ray holder and positioner 100 enables improving the comfort of the patient and improving the performance efficiency of the technician. To use the x-ray holder and positioner 100, the x-ray detector is placed within brackets 130A, 130B. Depending on the desired location of the x-ray detector, extending arm 115B is adjusted to a desired length, then arm screw 125 is tightened to hold the x-ray detector in place. Next, the angle of arm 115A, 115B is adjusted until the x-ray detector is in a position where the patient is comfortable, and the technician can perform the exam efficiently. Hinge screw 120 is tightened to hold the angle of the x-ray detector in place. As illustrated in FIG. 1, x-ray holder and positioner 100 can have an angular position of, for example, about 45-degrees and an extension of the full length of base arm 115A and the full length of extending arm 115B. After the exam has been completed, the angle and length of arm 115A, 115B are adjusted to the resting position (see FIG. 2, 0-degrees and no extension of extending arm 115B) of arm 115A, 115B and conveniently stored, for example, on the portable x-ray machine or in the x-ray room.

Figure 2:
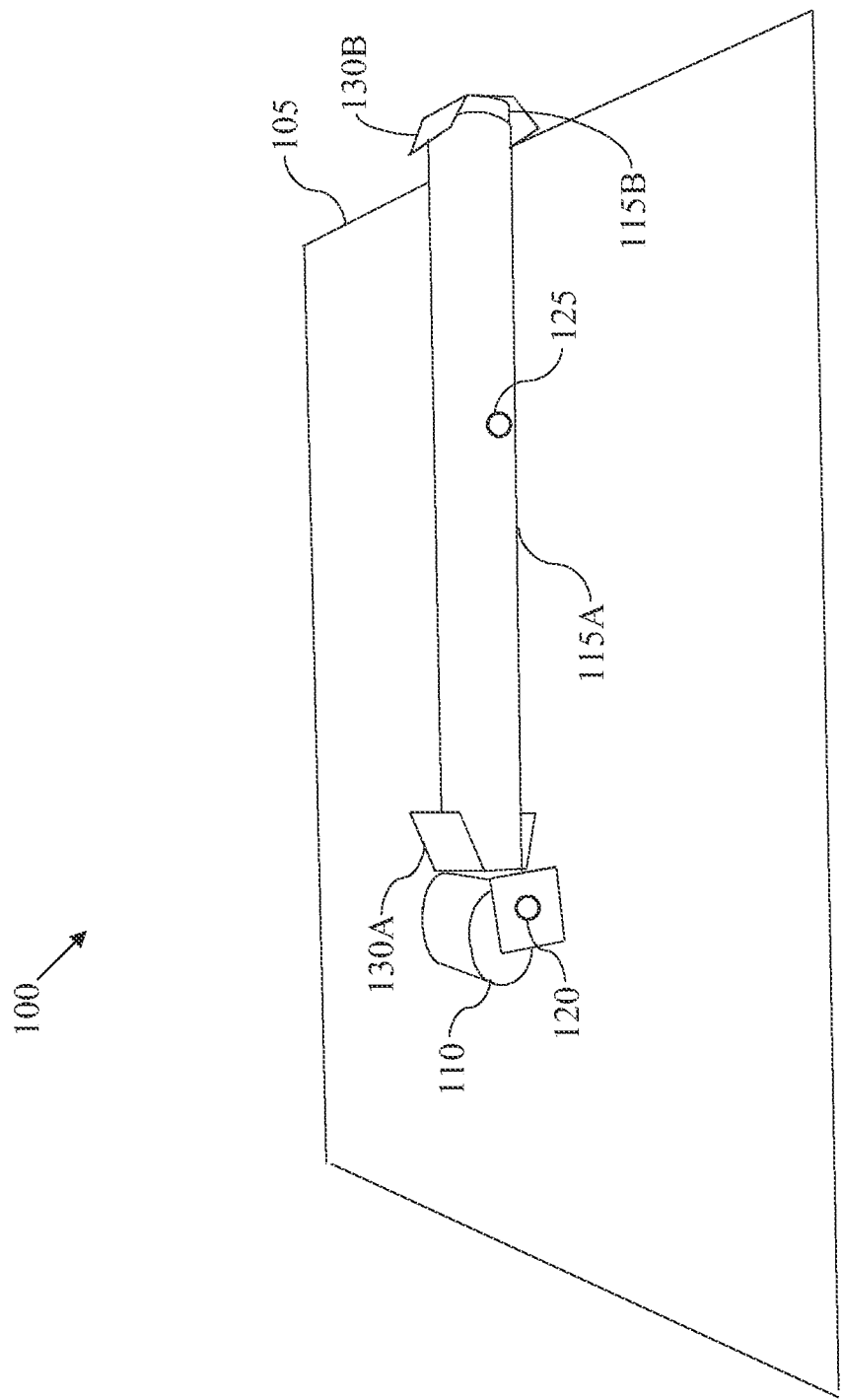
FIG. 2 illustrates a perspective view of the holder of FIG. 1, according to some embodiments.
Figure 3:
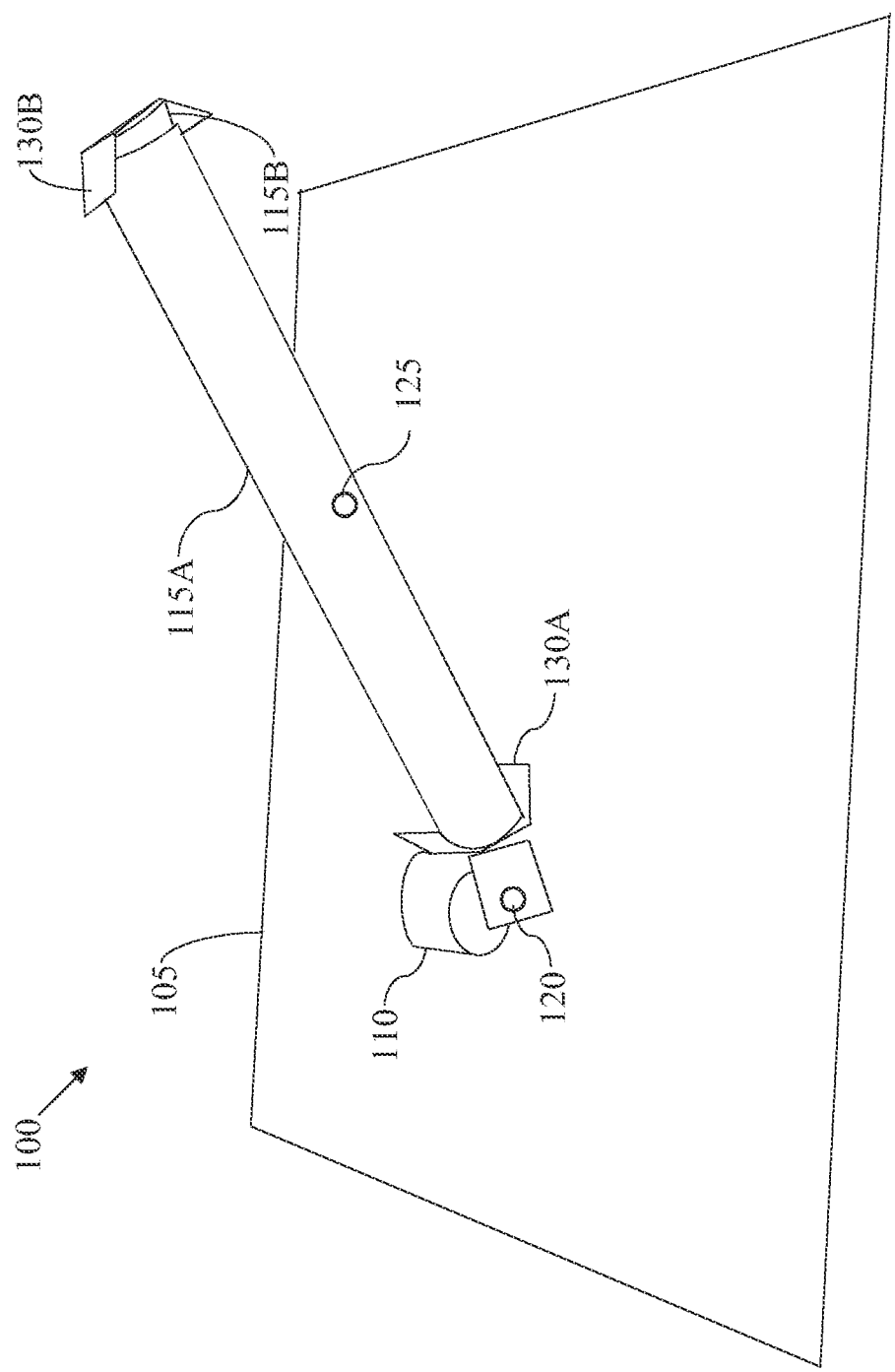
FIG. 3 illustrates a perspective view of the holder of FIG. 1, according to some embodiments.
Figure 4:
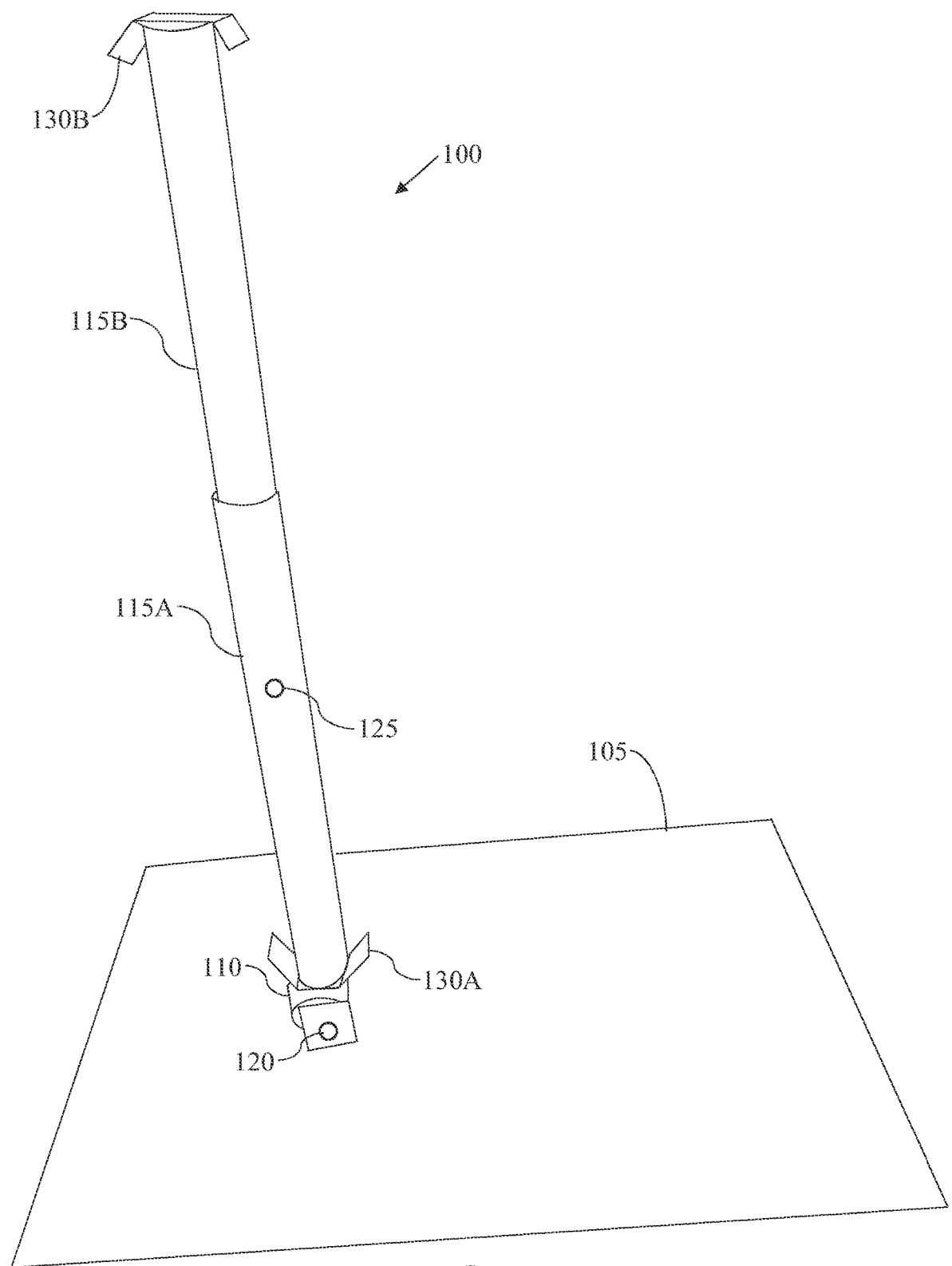
FIG. 4 illustrates a perspective view of the holder of FIG. 1, according to some embodiments.

Referencing FIG. 2 to FIG. 4 use of x-ray holder and positioner 100 is illustrated. As shown in FIG. 2, x-ray holder and positioner 100 can have a first configuration, or resting position, wherein X-ray holder and positioner 100 is at an angle of substantially 0-degrees relative to base 105 and extending arm 115B is substantially entirely enclosed along the length of extending arm 115B by base arm 115A. Usually in this configuration x-ray holder and positioner 100 is stored and/or transported.

Referencing FIG. 3, x-ray holder and positioner 100 is illustrated in another possible angular position of arm 115A, 115B. As shown, base arm 115A is at an angle of about 30- to 40-degrees relative to base 105. In the position illustrated, extending arm 115B remains substantially completely within base arm 115A; hence, arm 115A, 115B has no substantial extension beyond the length of base arm 115A.

Referencing FIG. 4, x-ray holder and positioner 100 is illustrated in another possible angular position and extension of arm 115A, 115B. As shown, base arm 115A is at an angle of substantially 90-degrees relative to base 105. In the position illustrated, extending arm 115B has been telescoped substantially completely out of base arm 115A; hence, arm 115A, 115B has substantially its full extension.

As illustrated in FIG. 1 through FIG. 4, x-ray holder and positioner 100 is configured to facilitate the placement of an x-ray detector at a desired angle and at a variable distance relative to base 105. Consequently, x-ray holder and positioner 100 improves both patient comfort and efficiency of obtaining radiologic images. As illustrated and described x-ray holder and positioner 100 can be positioned at any angle of, for example, between 0-degrees and 90-degrees, and the length of rotatable and extendable arm 115A, 115B can be extended to multiples of any suitable length for the task of obtaining radiologic images.

FIGS. 5-10 illustrates a second embodiment of the x-ray holder and positioner 100 which includes a first extending arm 500 and a second extending arm 501 extending in parallel from one another and having a mountable surface 503 secured to each of the first extending arm 500 and the second extending arm 501. The embodiment illustrated in FIGS. 5-10 provide similar benefits as the embodiment illustrated in FIGS. 1-4 while providing additional support for the x-ray holder and positioner 100 by adding a second extending arm 501.

Figure 5:
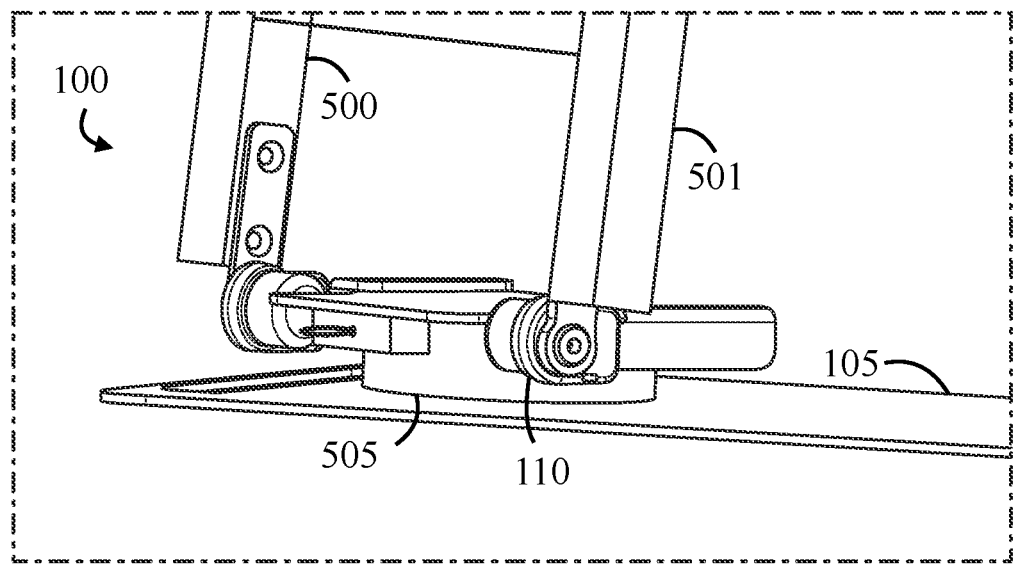
FIG. 5 illustrates a detail view of the pivot of the holder, according to some embodiments.
Figure 6:
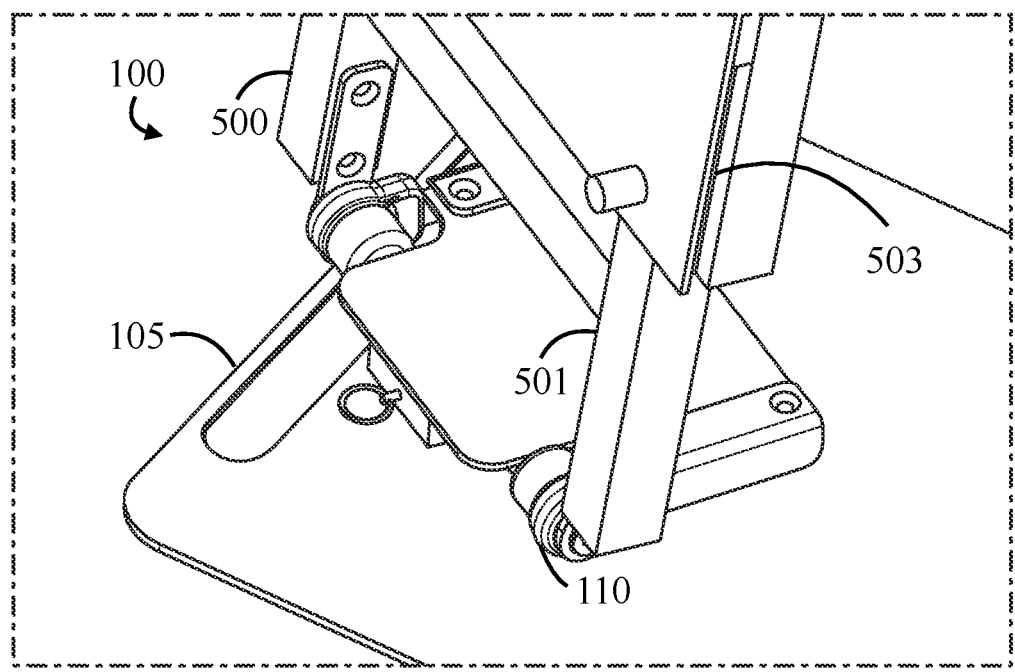
FIG. 6 illustrates a detail view of the pivot of the holder, according to some embodiments.

FIG. 5 and FIG. 6 illustrate a detail view of the hinge 110 illustrated in a second embodiments. of the x-ray holder and positioner 100. The hinge 110 is positioned between the base 105 and the first extending arm 500 and second extending arm 501 to allow them to hinge between 0° and 90° with reference to the base 105. A rotatable mount 505 allows for the first extending arm 500 and second extending arm 501, as well as the mounting surface 503 to rotate 360° such that the user can suitably position the x-ray detector as needed throughout use or for convenient storage.

Figure 7:
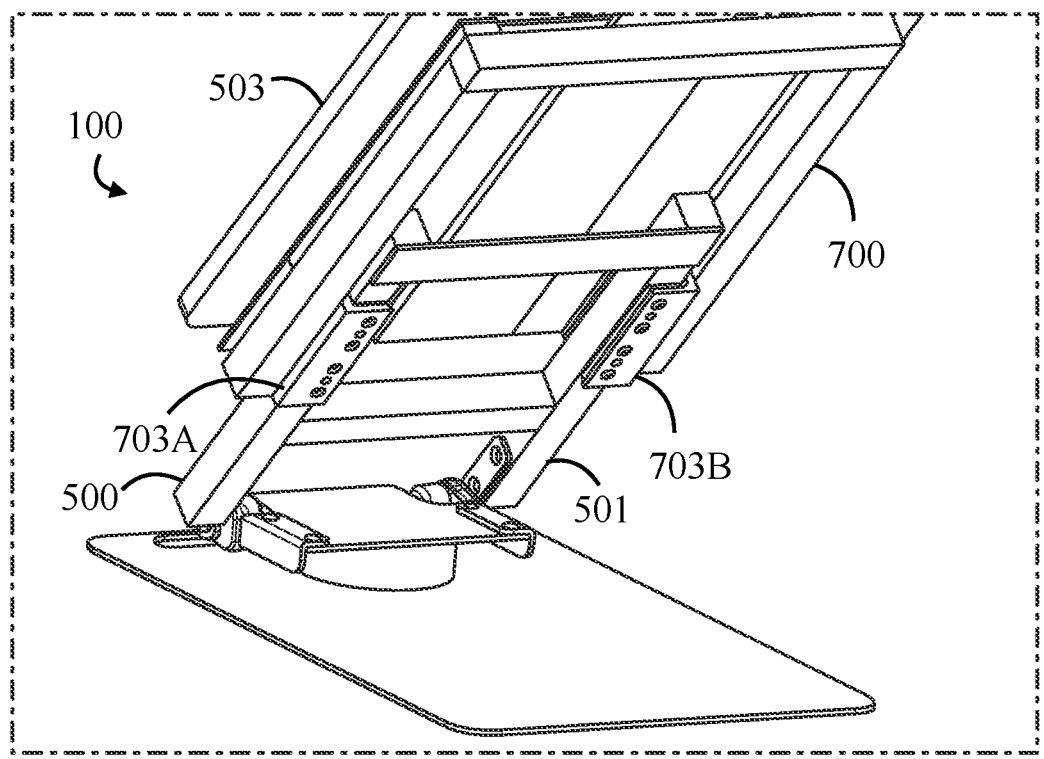
FIG. 7 illustrates a perspective view of the holder, according to some embodiments.
Figure 8:
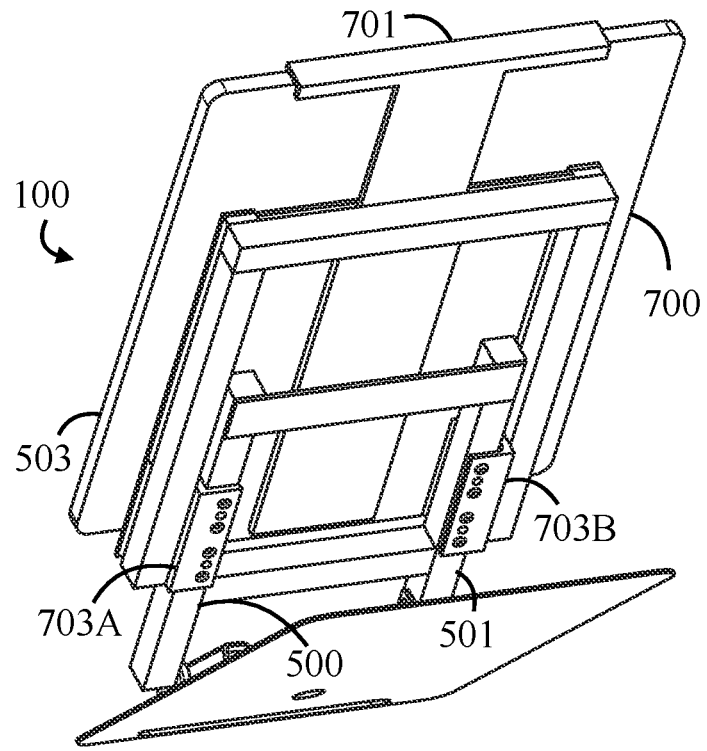
FIG. 8 illustrates a perspective view of the holder, according to some embodiments.

FIG. 7 and FIG. 8 illustrate a rear side 700 perspective view of the x-ray holder and positioner 100. In specific reference to FIG. 7, the mounting surface 503 interfaces with a retainer 701 to maintain the x-ray detector in a suitable position during use and/or during storage. The first extending arm 500 and the second extending arm 501 each include and extension assembly 703A, 703B which allow the arms to extend as needed.

Figure 9:
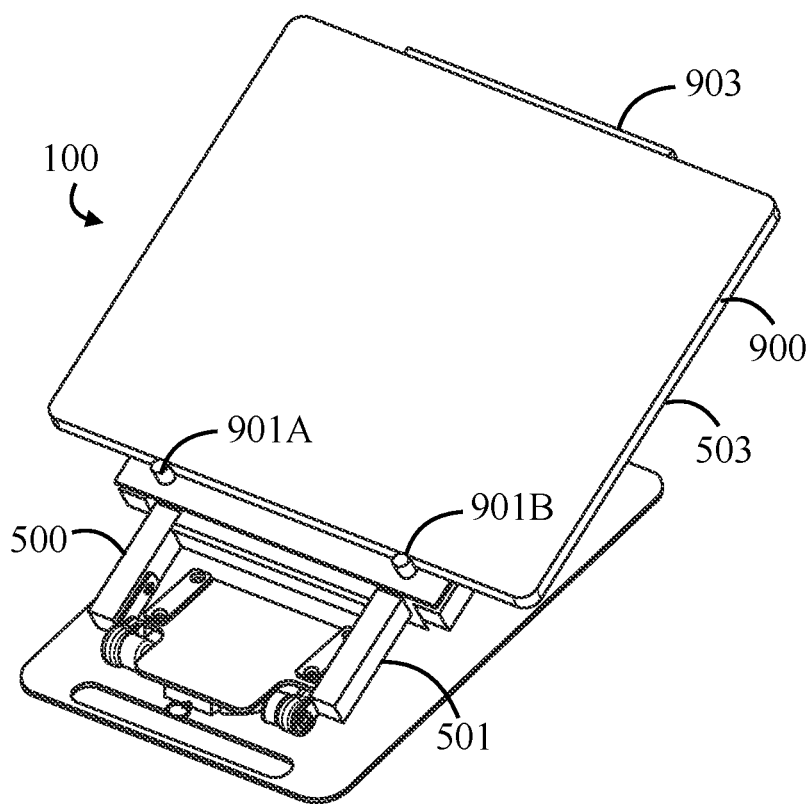
FIG. 9 illustrates a perspective view of the holder, according to some embodiments.
Figure 10:
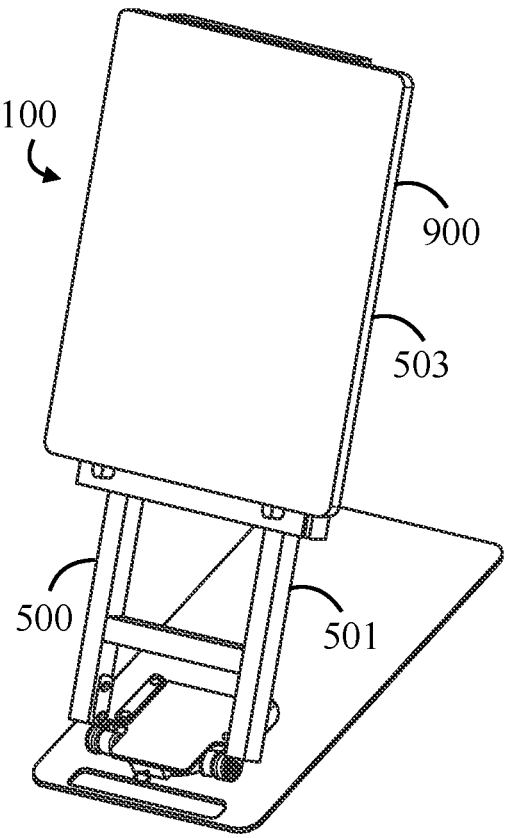
FIG. 10 illustrates a perspective view of the holder, according to some embodiments.

FIG. 9 and FIG. 10 illustrate a front side 900 perspective view of the x-ray holder and positioner 100. The mountable surface 503 is a component of an x-ray detector holding mechanism 905 coupled to each of the first ending arm 500 and the second extending arm 501. The mountable surface 503 retains the x-ray detector in a suitable positioned via a first pin 901A and a second pin 901B. A top retainer 903 may be extended or retracted to maintain the x-ray detector in a suitable position during use.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A portable x-ray detector holder and positioner comprising:
   a base plate;
   a hinge coupled to the base plate;
   a base arm coupled to the hinge;
   a fastening mechanism for facilitating an angular adjustment of the base arm relative to the base, wherein the fastening mechanism for facilitating an angular adjustment of the base arm is coupled to the base arm and/or to the hinge;
   an extending arm configured to be received in the base arm and to be telescoped out of the base arm;
   a fastening mechanism for facilitating a length adjustment of the extending arm relative to the base arm, wherein the fastening mechanism for facilitating a length adjustment of the extending arm relative to the base arm is coupled to the base arm and/or to the extending arm; and
   an x-ray detector holding mechanism coupled to the base arm and/or to the extending arm for holding an x-ray detector.

2. The modular portable x-ray detector holder and positioner of claim 1, wherein the fastening mechanism for facilitating an angular adjustment comprises a screw.

3. The portable x-ray detector holder and positioner of claim 1, wherein the x-ray detector holding mechanism comprises one or more brackets coupled to the base arm and/or to the extending arm.

4. The modular portable x-ray detector holder and positioner of claim 2, wherein the screw is selectively tightened or loosened to adjust a position of the base arm.

5. A method of obtaining radiologic images, the method comprising:
   providing an x-ray detector holder and positioner, the x-ray detector holder and positioner comprising:
   a base;
   a rotatable and extendable arm coupled to the base; and
   an x-ray detector holding mechanism coupled to said arm, wherein the x-ray detector holding mechanism comprises a fastening mechanism for facilitating a length adjustment of the extending arm relative to the base arm, wherein the fastening mechanism for facilitating a length adjustment of the extending arm relative to the base arm is coupled to the base arm and/or to the extending arm;

adjusting an angle of said arm to a desired angle;

adjusting a length of said arm to a desired length;

attaching an x-ray detector to said x-ray detector holding mechanism; and positioning the x-ray detector holder and positioner relative to a patient to facilitate obtaining the radiologic images.

6. The method of claim 5, wherein the x-ray detector holder and positioner further comprises a hinge coupled to said arm.

7. The method of claim 5, wherein the x-ray detector holding mechanism comprises at least one bracket coupled to said arm.

8. The method of claim 5, wherein said arm comprises a first structure configured to receive a second structure, and wherein the second structure is configured to be telescoped out of the first structure.

* * * * *